United States Patent [19]

Ignatius et al.

[11] Patent Number: 5,278,432
[45] Date of Patent: Jan. 11, 1994

[54] APPARATUS FOR PROVIDING RADIANT ENERGY

[75] Inventors: Ronald W. Ignatius; Todd S. Martin, both of Dodgeville, Wis.

[73] Assignee: Quantam Devices, Inc., Barneveld, Wis.

[21] Appl. No.: 936,570

[22] Filed: Aug. 27, 1992

[51] Int. Cl.$^5$ .......................................... H01L 33/00
[52] U.S. Cl. ........................................ 257/88; 257/99; 257/723; 362/800; 307/311
[58] Field of Search ................... 257/88, 98, 99, 723, 257/706, 918; 313/500, 512; 362/800; 307/311; 47/DIG.

[56] References Cited

U.S. PATENT DOCUMENTS

| | | | |
|---|---|---|---|
| 3,876,907 | 4/1975 | Widmayer | 315/208 |
| 3,930,335 | 1/1976 | Widmayer | 47/58 |
| 4,084,905 | 4/1978 | Schreiber et al. | 356/85 |
| 4,168,102 | 9/1979 | Chida et al. | 313/111 |
| 4,298,869 | 11/1981 | Okuno | 257/99 |
| 4,603,496 | 8/1986 | Latz et al. | 40/547 |
| 4,628,422 | 12/1986 | Ewald | 362/240 |
| 4,650,336 | 3/1987 | Moll | 356/417 |
| 4,700,210 | 10/1987 | Burton et al. | 257/96 |
| 4,742,432 | 5/1988 | Thillays et al. | 361/400 |
| 4,749,916 | 6/1988 | Yamazaki et al. | 315/254 |
| 4,935,665 | 6/1990 | Murata | 313/500 |
| 5,012,609 | 5/1991 | Ignatius et al. | 47/58 |

FOREIGN PATENT DOCUMENTS

| | | | |
|---|---|---|---|
| 52-57731 | 5/1977 | Japan | 313/500 |
| 57-95683 | 6/1982 | Japan | 257/99 |
| 58-194383 | 11/1983 | Japan | 257/99 |
| 61-48982 | 3/1986 | Japan | 257/88 |
| 61-75571 | 4/1986 | Japan | 257/88 |
| 63-124479 | 5/1988 | Japan | 257/88 |
| 1-86573 | 3/1989 | Japan | 257/98 |
| 3-44080 | 2/1991 | Japan | 257/99 |

OTHER PUBLICATIONS

Li-Cor, "LI6200 Portable Photosynthesis System", 1989.
Campbell Scientific, Inc., "MPH-1000 Gas Exchange System", Published Mar., 1982.
"To Catch The Light: A Concise History of Photoelectronic Sensing", Product Design and Development, Nov., 1988, pp. 49 and 52, Garwood.
Hoehn, Alex et al., "LED—A Challenging Opportunity . . . ", present at the American Soc. for Gravitational Space Biology, Coco Beach, Fla., 1989.
Barta, D. J. et al., "Evaluation of Light Emitting . . . ", Adv. Space Res., vol. 12, No. 5 pp. (5) 141–(5) 149, 1992.
Hoehn, Alexander, "Lighting Considerations for Artifical . . . ", presented at the Fourth European Symposium Life Science Research in Space, May–Jun., 1990, Trieste, Italy, pp. 1, 20–22 and 27.

Primary Examiner—William Mintel
Assistant Examiner—Minhloan Tran
Attorney, Agent, or Firm—Andrus, Sceales, Starke & Sawall

[57] ABSTRACT

The monolithic hybrid LED array includes a metal heat sink substrate, a ceramic layer on the substrate, and a plurality of series-connected epitaxially-formed LEDs connected by interconnects such as conductive ink strips. The array preferably includes three to six sets of series-connected LEDs that are tightly packed on the substrate. The LEDs are housed in a modular housing having a power regulating circuit and an override feature for overriding the regulator to produce the maximum LED output for brief periods of time. The regulator may continuously vary the light intensity output from the equivalent of 0 to 2000 micromols per second per meter squared.

33 Claims, 5 Drawing Sheets

APPARATUS FOR PROVIDING RADIANT ENERGY

BACKGROUND OF THE INVENTION

This invention relates to apparatus for providing radiant energy to enhance and test plant growth, and more particularly to apparatus that uses optoelectronic devices such as light emitting diodes to provide such radiant energy.

Several types of devices are known for providing radiant energy to enhance and test plant growth. Typical prior art electrical light sources include fluorescent, high pressure sodium, and other metal halide lamps. These prior art devices have several major disadvantages.

One disadvantage of metal halide lamps is that they provide a great deal of infrared and/or heat energy. Excessive infrared and heat energy has a deleterious effect on plants. To overcome this disadvantage, typical prior art devices must be placed at a sufficient distance from the plant to prevent plant damage. When the device is being used with a leaf chamber to test the ability of the plant to transform the radiant energy into chemical energy, extensive additional apparatus is required to remove the infrared and heat energy to prevent harm to the leaf. The use of such additional cooling and ventilating apparatus greatly increases the effective cost of the radiant energy.

Another disadvantage of metal halide energy sources is that the light intensity cannot be continuously reduced to a zero intensity since metal halide lamps require a minimum voltage to maintain the arc in the lamp. Since it is often desirable to reduce the energy output to a zero or a near zero intensity, the metal halide lamps are not suitable for some applications.

Typical prior art metal halide and other electrical energy sources output light having a relatively broad spectrum. However, it has been found that plant growth does not require the full spectrum of visible light. Thus, it is desirable to provide radiant energy sources that emit radiation in one or more specific regions of the spectrum.

U.S. Pat. No. 5,012,609 issued May 7, 1991 to Ignatius et al discloses an array of light emitting diodes which provide radiant energy in specific regions of the spectrum. However, a light emitting diode array like that disclosed in U.S. Pat. No. 5,012,609 requires a plurality of discrete light emitting diodes that must be plugged into a circuit. That arrangement limits the number of light emitting diodes that may be packed into the array. It is also somewhat expensive to manufacture and assemble an array of light emitting diodes using discrete components. Also, the power requirements for such arrays, as well as for metal halide lamps, are relatively large, increasing the cost of operation of the electrical energy sources.

SUMMARY OF THE INVENTION

A unique hybrid monolithic array of opto-electronic devices such as light emitting diodes or cold cathode fluorescent devices is disclosed that may be used to enhance and test plant growth as well as to irradiate samples of other types of living cells.

In a preferred embodiment, the array includes a thermally conductive substrate made of aluminum or copper that acts as a heat sink. Disposed on top of the substrate is a substantially non-electrically conductive ceramic layer. A plurality of epitaxially-formed, double heterojunction, double power light emitting diodes (LEDs) are bonded to the ceramic layer. The LEDs are preferably formed of a gallium aluminum arsenide material so that they emit substantially monochromatic light having 620–680 and/or 700–760 nm wavelengths that are particularly r desirable for plant growth. The array may also include silicon carbide LEDs that emit substantially monochromatic light have a 400–500 nm wavelength.

The array may contain multiple sets of series-connected LEDs. In each set of LEDs, adjacent LEDs are electrically connected by interconnects such as conductive strips deposited on the ceramic layer. The interconnects are preferably made from a metal-containing ink, although they could consist of a metal lead frame or wires. The array is arranged such that a first electrode of a first LED is electrically connected to one end of the interconnect. The opposite end of the interconnect is electrically connected to an opposite polarity electrode of an adjacent, series-connected LED, preferably by a standard wire. The body of each LED, including its heterojunctions, is preferably substantially encased in a passivation material, and is bonded to the ceramic layer using an electrically-conductive epoxy adhesive. The entire array is coated with a conformal coating of a transparent epoxy material to protect it during handling.

In a preferred embodiment, each set of series-connected LEDs includes 34 LEDs disposed on a one inch by two inch substrate. However, the LEDs may be so tightly packed that each set of series-connected LEDs may include three hundred or more LEDs. The array preferably includes six sets of LEDs in a modular housing, although any number of sets or modules may be used in a particular application. In the preferred embodiment, two adjacent sets of LEDs are connected in series to yield an LED string of 68 LEDs. Three LED strings are connected in parallel to a DC power supply.

The LED array is preferably used in a modular housing that supports the array and that includes a cooling means such as a fan or an active heat sink for cooling the interior of the housing. A current regulator is capable of continuously varying the current to the array so that the emitted light from the array is equivalent to between about 0 to 2000 micromols per second per meter squared. The array is preferably covered with a glass cover to protect it from the environment.

The apparatus also preferably includes a means for briefly overriding the current regulator to provide maximum light output for a short period of time, on the order of 0.3 to 2 seconds. This override mode may be used to test for fluorescence of a plant leaf in a leaf chamber.

The array according to the present invention includes a number of features and advantages not found in prior art electrical energy sources. First, the array is inexpensive to manufacture using readily-available semiconductor chip manufacturing techniques, thereby avoiding the need to plug discrete LED components into a circuit board as in prior art devices. Second, the LEDs in the present array may be very tightly packed to achieve a light intensity output with minimal heat output when compared to metal halide and similar prior art devices.

A third advantage is that the LEDs may output the full spectrum of visible light, or may output any selected band or bands of monochromatic light as desired.

Yet another advantage is that the light intensity may be continuously varied from a zero output up to a maximum output, which may equal or exceed the equivalent of one sun output (2000 micromols per second per meter squared) from an array that is only 3 inches by 4 inches in size.

The housings in which the arrays are disposed may be used separately or as modular components of a larger system. Each modular unit draws approximately 45 watts of power, compared to metal halide lamps which draw between about 150 to 1000 watts.

Other features and advantages of the present invention will be apparent to those skilled in the art from the following detailed description of the preferred embodiments and the attached drawings, in which:

DETAILED DESCRIPTION OF THE PREFERRED EMBODIMENTS

Figure 1:
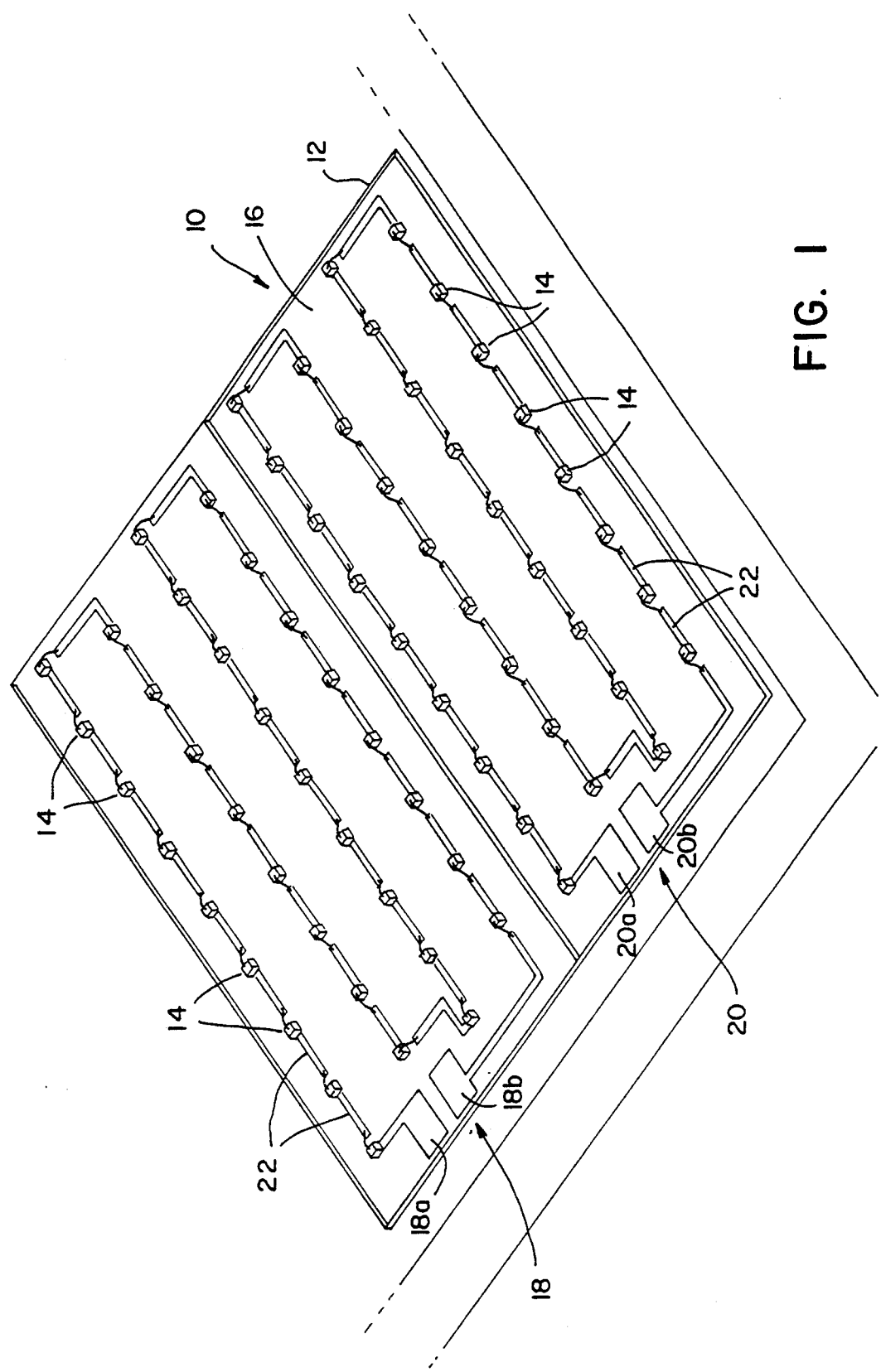
FIG. 1 is a perspective view of an LED array according to the present invention.

FIG. 1 depicts an array of light emitting diodes (LEDs) according to the present invention though the description herein refers to LEDs, it is to be understood that other optoelectronic devices may be used, such as cold cathode fluorescent devices In FIG. 1, array 10 includes an aluminum or copper-coated substrate 12 that acts as a heat sink for heat generated by LEDs 14. A layer 16 of a substantially non-electrically conductive material is formed on substrate 12. Layer 16 is preferably made of a ceramic material, although other materials may be used.

Figure 4:
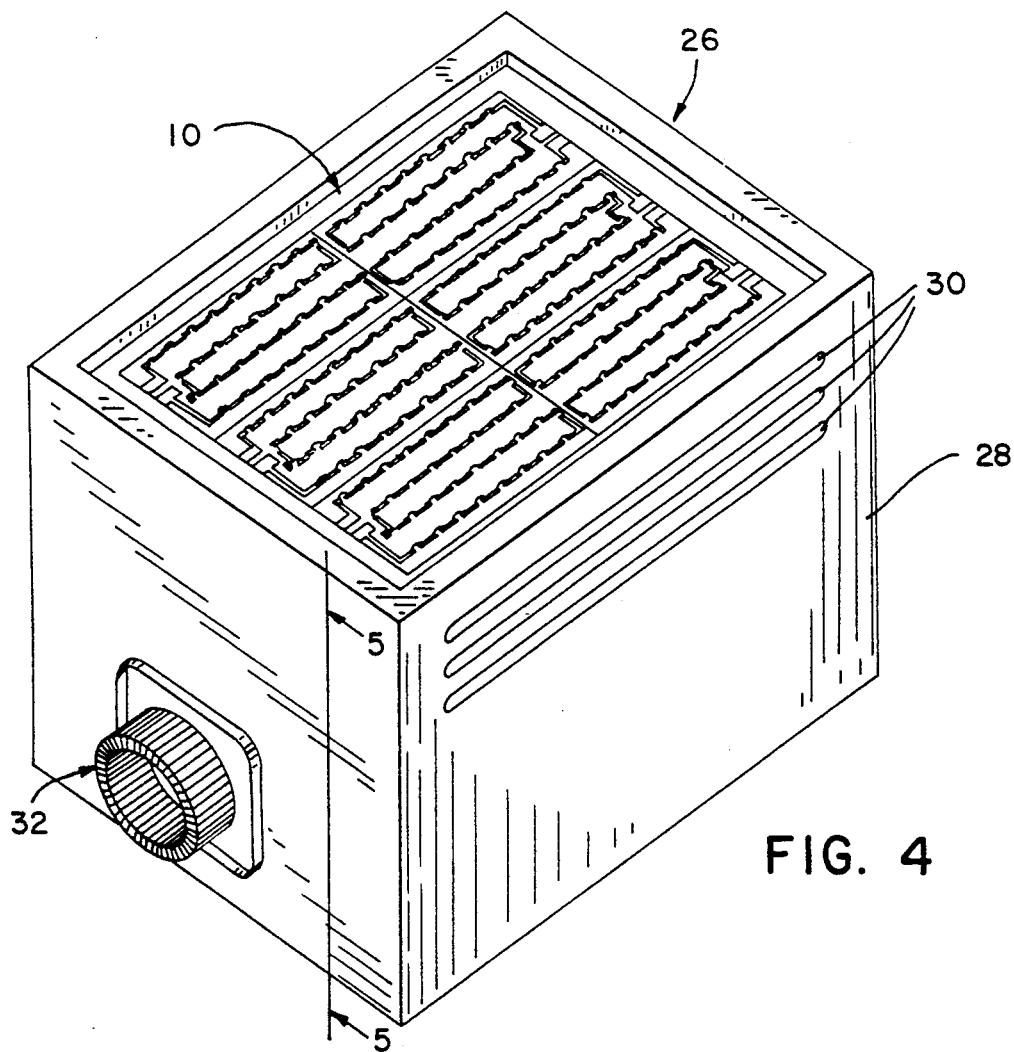
FIG. 4 is a perspective view of a modular housing according to the present invention.

LEDs 14 are preferably grouped into a plurality of sets 18 and 20, with the LEDs in each set being series-connected. Each of sets 18 and 20 preferably occupies a one inch by two inch area of substrate 12, so that adjacent sets 18 and 20 occupy a two inch by two inch square area. This arrangement allows a commercially available extruded aluminum heat sink to be used for substrate 12. Sets 18 and 20 are preferably connected in series to yield an LED string of series-connected LEDs 14. Array 10 may consist of any number of sets of LEDs, with six sets of LEDs being preferred in a single modular housing, as depicted in FIG. 4.

As discussed below in connection with FIG. 6, each set 18 and 20 has two contacts. Set 18 has contacts 18a and 18b. Set 20 has contacts 20a and 20b. DC power is applied to contacts 18a and/or 20a, depending upon whether sets 18 and 20 are connected in series or in parallel to each other. The current through the LEDs is regulated by control signals applied to contacts 18b and/or 20b.

As depicted in FIG. 1, each of sets 18 and 20 includes 34 LEDs 14. However, the LEDs may be much more tightly packed, so that up to 300 or more LEDs may be series-connected into a single set.

Figure 2:
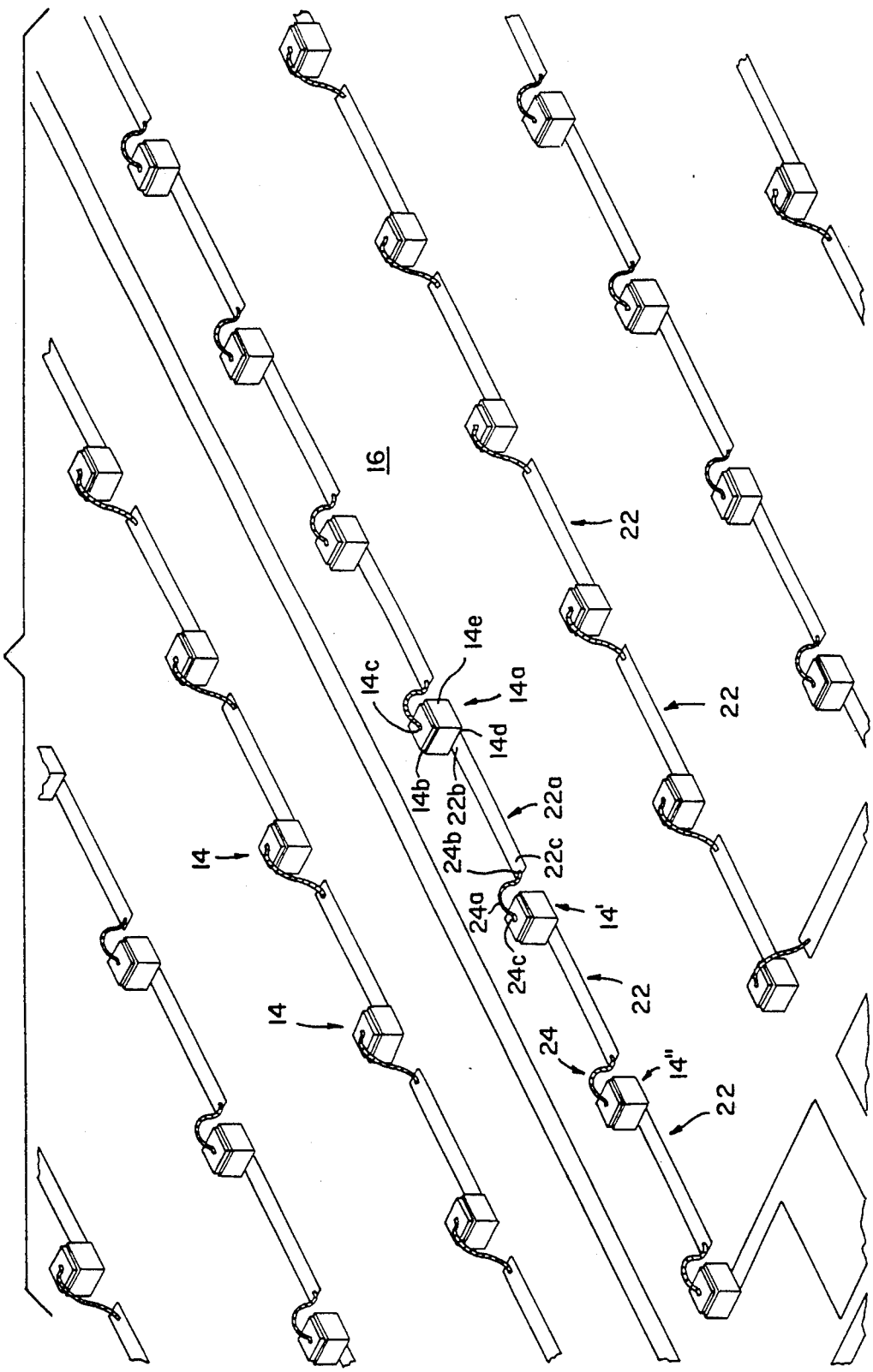
FIG. 2 is an exploded perspective view of a portion of the array of FIG. 1.
Figure 3:
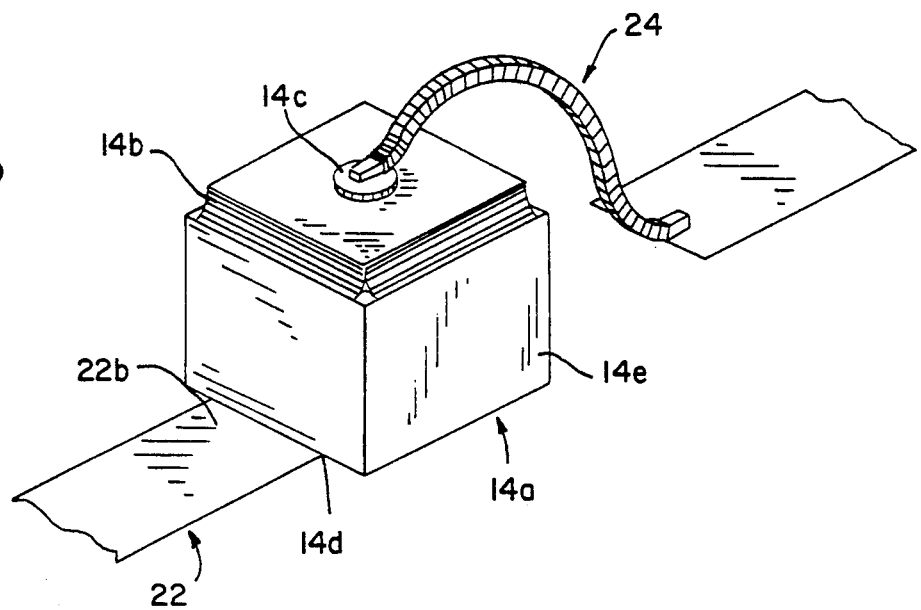
FIG. 3 is a perspective view of a single light emitting diode and adjacent conductive strips.

The manner in which the LEDs are connected to each other is more clearly depicted in FIGS. 2 and 3. In FIGS. 2 and 3, an exemplary LED 14a includes a substantially transparent double heterojunction 14b, an electrode 14c, and a cathode electrode 14d. The electrodes may be reversed so that electrode 14c is a cathode and electrode 14d is an anode, depending upon the choice of manufacturer for LED 14a. Heterojunction 14b is preferably made from a material containing gallium aluminum arsenide that is applied in epitaxial layers. Gallium aluminum arsenide is particularly suitable to yield a monochromatic light emission output in 620–680 and/or 700–760 nanometer ranges. Silicon carbide could be used to achieve a range of between 400–500 nm wavelength. The GaAlAs LEDs are preferably made by Mitsubishi Kaisi Polytech of Japan, and are available from Showa Denkoa or Stanley, both of Japan, or from Hewlett-Packard of Palo Alto, Calif. The silicon carbide LEDs are available from Cree Research Inc., Durham, N.C.

Heterojunction 14b is preferably encased in a passivation material 14e and is bonded to ceramic layer 16 using an electrically-conductive epoxy. One suitable epoxy adhesive is made by Ablestik of Rancho Dominquez, Calif., sold under the trademark ABLEBOND, Type No. 84-1LMIT. Ceramic layer 16 is preferably 10 mils thick, and is bonded to substrate 12 using a conductive epoxy made by Ablestik, sold under the trademark ABLEBOND, Type No. 789-4. Heat is transferred through ceramic layer 16 to the heat sink substrate 12.

Adjacent, series-connected LEDs 14 are connected to each other by means of electrically-conductive interconnects, such as strips 22 and standard wires 24. Strips 22 are preferably made from a metal ink. Other interconnects may be used in place of strips 22, such as a metal lead frame or metal wires.

In FIG. 2, strip 22a has a first end 22b that is electrically connected to cathode 14d, and an opposite second end 22c that is connected to one end 24b of wire 24a. The opposite end 24c of wire 24a is connected to the anode of an adjacent LED 14'. LED 14' and LED 14", as well as the other series-connected LEDs 14 in array 10, are connected to each other in a manner similar to that discussed above in connection with LEDs 14a and 14'. FIG. 3 more clearly depicts the components of LED 14a.

The array of LEDs discussed above in connection with FIGS. 1 through 3 is preferably used to enhance or test plant growth. In these applications, LEDs 14 are preferably monochromatic, or output several narrow bands of spectral radiation, as disclosed in U.S. Pat. No. 5,012,609 to Ignatius et al., which patent is incorporated by reference herein. However, the LED array may have other applications, such as the irradiation of animal or human tissue. In the latter applications, the LEDs may be selected to provide different ranges of spectral emissions, as desired.

Figure 5:
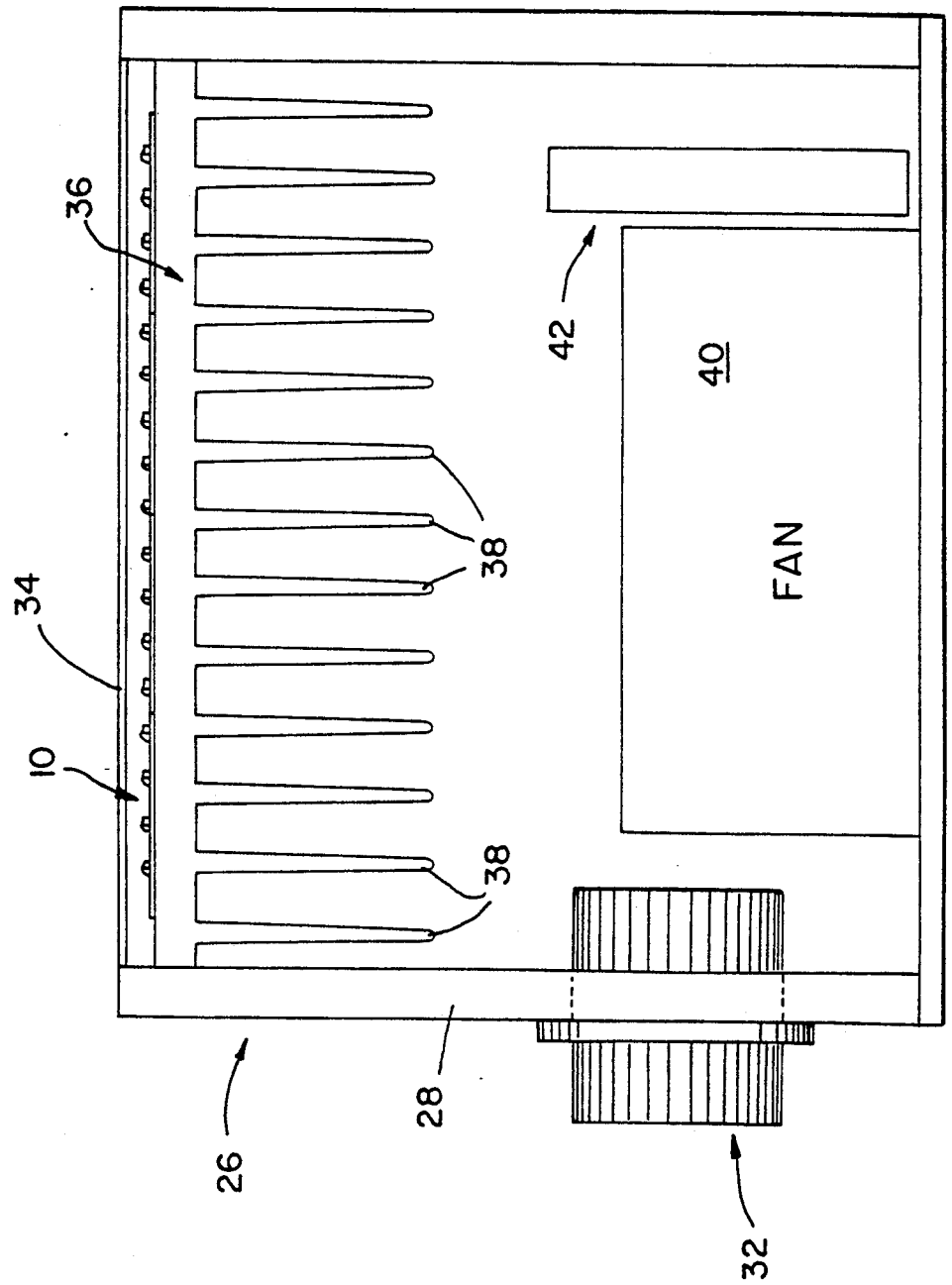
FIG. 5 is a cross sectional side view of the modular housing, taken along line 5—5 of FIG. 4.

FIGS. 4 and 5 depict LED array 10 being housed in a modular unit 26 that is particularly suitable for enhancing plant growth. These modular units may be connected in parallel to provide a large scale artificial lighting environment for plants.

In FIGS. 4 and 5, modular unit 26 includes a housing 28 that supports LED array 10. A plurality of air vents 30 are formed in at least one side of housing 28. Modular unit 26 also includes a connector 32 that is adapted to receive a power cord from a power supply unit (not shown). Connector 32 is preferably a 16 pin connector, although only 10 pins are used in the embodiment discussed herein.

FIG. 5 is a side cross sectional view of modular unit 26, taken along line 5—5 of FIG. 4. In FIG. 5, modular unit 26 includes a glass cover plate 34 that protects LED array 10 from the environment. Disposed directly below LED array 10 is an internal heat sink 36 that has a plurality of fins or vanes 38 from which heat generated by LED array 10 is dissipated. An internal fan 40 pulls the heat from the interior of housing 28 and propels it into the environment.

Also disposed within housing 28 is a circuit board 42 that contains at least some of the components of the internal DC power supply, the current regulator, and override circuit discussed below in connection with FIG. 6. The remaining electronics may be contained in a separate control unit.

Figure 6:
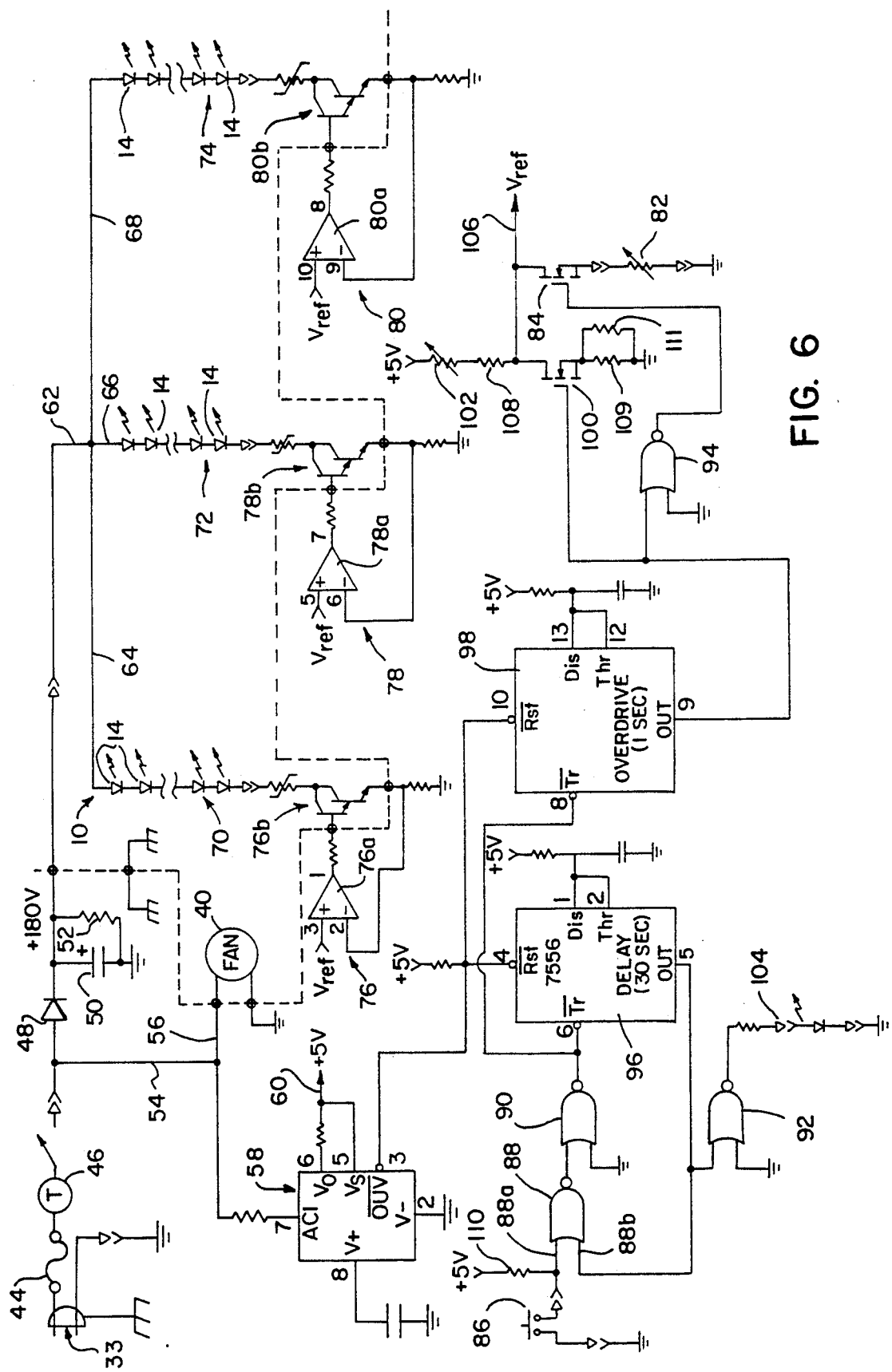
FIG. 6 is a schematic diagram depicting the power supply, the current regulator, and the override means of the invention.

In FIG. 6, 120 VAC is input to the circuits at connector 33. A fuse 44 and a current limiter 46 protect the electronics from power surges, voltage spikes and the like. The input AC waveform is rectified by a half-wave rectifier consisting of diode 48, capacitor 50, and resistor 52. The output from the rectifier is +180 V direct current. The unrectified AC signal is used to power fan 40 via lines 54 and 56. The AC signal is also used to drive a converter 58, whose output on line 60 is +5 VDC that is used to drive the circuit logic.

The +180 VDC is input to LED array 10 via lines 62, 64, 66, and 68. In the preferred embodiment described herein, the LED array, consisting of 6 sets of series-connected LEDs 14, is divided into 3 LED strings 70, 72, and 74, with the LEDs in each string being series-connected. Two adjacent LED sets are connected in series to form each LED string. LED strings 70, 72, and 74 are connected to each other in parallel.

The current through LED strings 70, 72, and 74 is precisely controlled by a constant current regulator consisting of circuits 76, 78, and 80 respectively. Regulator circuit 76 includes an operational amplifier 76a whose positive input is a voltage reference signal Vref that is derived as discussed below. The output of amplifier 76a controls the gating of a Darlington transistor pair 76b which in turn controls the current through LED string 70. The emitter of Darlington pair 76b is connected to the negative input of amplifier 76a to provide current feedback, as is well known in the art.

Current regulator circuits 78 and 80 have similar configurations to current regulator circuit 76. Regulator circuit 78 includes an operational amplifier 78a whose positive input is the signal Vref, and whose negative input is the feedback signal from Darlington transistor pair 78b. Operational amplifier 78a controls the gating of transistor pair 78b, which in turn precisely controls the current through LED string 72.

Similarly, regulator circuit 80 includes an operational amplifier 80a whose positive input receives the signal Vref, and whose negative input receives a current feedback signal from the emitter of a Darlington pair 80b. Darlington transistor 80b controls the current through LED string 74.

The voltage reference signal Vref that is used to regulate the current in the LEDs is derived from the manual setting of a continuously variable pot switch 82 located on the front panel of the control unit. Switch 82 is continuously variable from 0 to 100 milliamps. Switch 82 is connected in series with the source of a normally ON field effect transistor (FET) 84. When switch 84 is ON, the setting of switch 82 forms a voltage divider between the full scale calibration pot switch 102 and resistor 108 to determine the Vref signal, the latter varying from 0 volts (corresponding to 0 milliamps) to 1 volt (corresponding to a 100 milliamp setting of switch 82).

The present invention also includes a means for briefly overriding the setting of switch 82 to achieve a maximum or "overdrive" output from the LED array for a brief period of time, on the order of 0.3 to 2 seconds. In the embodiment discussed herein, the setting of switch 82 is overridden for a period of 1 second. This feature may be used to test the fluorescence of a plant leaf by placing the leaf in a leaf chamber (not shown) in close proximity to array 10 of modular unit 26.

In FIG. 6, the override circuit includes a front panel switch 86, NOR gate 88, inverters 90, 92 and 94, a 556 timer (depicted as dual 555 timers 96 and 98), an FET 100, resistors 109 and 111, and a pot switch 102 which is calibrated to full scale.

The override circuit operates as follows. When switch 86 is pressed, input 88a of NOR gate 88 is brought to a low state. Since input 88b is also in a low state when switch 86 is depressed for the first time, the output of gate 88 becomes a high input to gate 90, which is connected as an inverter. The output of inverter 90 goes low, triggering delay circuit 96 and overdrive circuit 98.

After the override circuit has been successfully triggered, delay circuit 96 outputs a high state signal at pin 5 for 30 seconds to prevent the retriggering of the circuit, regardless of whether switch 86 is pressed during that delay period. Delay circuit 96 outputs a high state signal to input 88b of NOR gate 88, causing the output of NOR gate 88 and the input to inverter 90 to go low. The output of inverter 90 goes high, thereby preventing the triggering of overdrive circuit 98 during the delay period.

The high state signal from pin 5 of delay circuit 96 is inverted by inverter 92, causing LED 104 to remain OFF. LED 104 is a front panel light which indicates whether the override mechanism is in the Ready state.

After pin 8 of overdrive circuit 98 receives a low going trigger signal, overdrive circuit 98 outputs at pin 9 a high state signal to gate ON FET 100. The gating ON of FET 100 switches resistors 109 and 111 to line 106 to form a voltage divider between full scale calibration pot 102 and resistor 108, resulting in a maximum value for the voltage reference signal Vref. Regulator circuits 76, 78, and 80 then allow maximum current to flow through their respective LED strings 70, 72 and 74.

The high state signal output at pin 9 of overdrive circuit 98 is inverted by inverter 94, the latter outputting a low state signal to turn OFF FET 84. The turning OFF of FET 84 deactivates pot switch 82 for a 1 second time period during the operation of the override circuit.

After the 30 second delay period has ended, input 88b to NOR gate 88 goes low. Input 88a to NOR gate 88 is high as a result of pull-up resistor 110. The output of NOR gate 88 is thus low, and the output of inverter 90 goes high, thereby preventing the triggering of delay circuit 96 and overdrive circuit 98 until switch 86 is activated again.

Although several preferred embodiments of the present invention have been shown and described, other embodiments will be apparent to those skilled in the art and are within the intended scope of the present inven-

We claim:

1. An array of optoelectronic devices comprising:
   a thermally-conductive substrate;
   a substantially non-electrically conductive layer disposed on said substrate;
   a first optoelectronic device disposed on said layer, including
      at least one first heterojunction;
      a first electrode interconnected with said first heterojunction;
      a second electrode interconnected with said first heterojunction;
   a second optoelectronic device disposed on said layer and connected in series with said first optoelectronic device, said second optoelectronic device including
      at least one second heterojunction;
      a third electrode interconnected with said second heterojunction;
      a fourth electrode interconnected with said second heterojunction;
   a first electrically-conductive interconnect disposed above said substantially non-conductive layer having a first end in electrical connection with said first electrode and having an opposite interconnect end in electrical connection with said fourth electrode;
   a regulator that is adapted to continuously vary the output of said first and second optoelectronic devices; and
   override means for briefly overriding said regulator to thereby briefly increase the output of said first and second optoelectronic devices.

2. The array of claim 1, wherein said thermally-conductive substrate is made from a material containing a metal.

3. The array of claim 2, wherein said metal is aluminum or copper.

4. The array of claim 1, wherein said substantially non-electrically conductive material includes a ceramic material.

5. The array of claim 1, wherein said electrically-conductive interconnect is made from a conductive ink.

6. The array of claim 1, further comprising:
   a wire connected between said opposite interconnect end and said fourth electrode.

7. The array of claim 1, wherein said at least one first heterojunction includes two heterojunctions.

8. The array of claim 1, wherein said first heterojunction includes a plurality of epitaxial layers.

9. The array of claim 1, wherein said first and second optoelectronic devices are substantially monochromatic.

10. The array of claim 9, wherein said monochromatic devices have a peak wavelength emission in the range of 620 to 680 nanometers.

11. The array of claim 1, wherein said first heterojunction is substantially enclosed in a passivation material.

12. The array of claim 1, wherein said first heterojunction is made from a material containing at least one of gallium aluminum arsenide and silicon carbide.

13. The array of claim 1, further comprising:
   a protective coating disposed on said first and second optoelectronic devices and on said interconnect.

14. The array of claim 1, wherein said first and second optoelectronic devices are light emitting diodes.

15. The array of claim 1, wherein said first electrode and said third electrode have a first polarity, and wherein said second electrode and said fourth electrode have a second polarity opposite to said first polarity.

16. The array of claim 1, further comprising:
   a third optoelectronic device connected in series with said second optoelectronic device, including a fifth electrode and a sixth electrode;
   a second electrically-conductive interconnect disposed above said layer having a first end in electrical connection with said third electrode and having an opposite second interconnect end in electrical connection with said sixth electrode.

17. The apparatus of claim 1, wherein said override means includes:
   means for providing maximum output of said first and second optoelectronic devices for a period of 0.3 to 2 seconds.

18. An apparatus that provides radiant energy to at least one living cell, comprising:
   a housing;
   an array of optoelectronic devices disposed within and supported by said housing, said array including
      a thermally-conductive substrate;
      a substantially non-electrically conductive layer disposed on said substrate;
      a first optoelectronic device disposed on said layer and having a first electrode and a second electrode;
      a second optoelectronic device disposed on said layer and having a third electrode and a fourth electrode;
      a conductive interconnect disposed above said layer having one end electrically connected to said first electrode and having an opposite end electrically connected to said fourth electrode;
   a power source that supplies power to said array;
   a regulator that is adapted to continually vary the energy emitted from said array; and
   override means for briefly overriding said regulator to thereby briefly increase the energy emitted by said array.

19. The apparatus of claim 18, wherein said first and second optoelectronic devices are light emitting diodes.

20. The apparatus of claim 18, wherein said first electrode and said third electrode have a first polarity, and wherein said second electrode and said fourth electrode have a second polarity opposite to said first polarity.

21. The apparatus of claim 18 wherein said housing has an interior, said apparatus, further comprising:
   cooling means for removing heat from the interior of said housing that was transferred from said optoelectronic devices through said thermally-conductive substrate.

22. The apparatus of claim 21, wherein said cooling means includes a fan interconnected with said housing.

23. The apparatus of claim 18, wherein said power source is a DC power supply.

24. The apparatus of claim 18, wherein said radiant energy includes emitted light, and wherein said regulator is adapted to continuously vary said emitted light from between 0 to 2000 micromols per second per meter squared.

25. The apparatus of claim 18, wherein said override means includes:

means for providing maximum energy output for a period of 0.3 to 2 seconds.

26. The apparatus of claim 18, further comprising:
a glass cover disposed above said array and supported by said housing.

27. The apparatus of claim 18, wherein said array includes a plurality of sets of optoelectronic devices, each of said sets having at least two series-connected optoelectronic devices connected by a conductive interconnect.

28. The apparatus of claim 18, wherein said thermally-conductive substrate is made from a material containing a metal.

29. The apparatus of claim 18, wherein said substantially non-electrically conductive material includes a ceramic material.

30. The apparatus of claim 18, wherein said electrically-conductive interconnect is made from a conductive ink.

31. The apparatus of claim 18, wherein said first and second optoelectronic devices are substantially monochromatic.

32. The apparatus of claim 31, wherein said monochromatic devices have a peak wavelength emission in the range of 620 to 680 nanometers.

33. The apparatus of claim 18, further comprising:
a protective coating disposed on said first and second optoelectronic devices and on said conductive interconnect.

* * * * *

UNITED STATES PATENT AND TRADEMARK OFFICE
CERTIFICATE OF CORRECTION

PATENT NO. : 5,278,432
DATED : January 11, 1994
INVENTOR(S) : Ronald W. Ignatius, et al It is certified that error appears in the above-indentified patent and that said Letters Patent is hereby corrected as shown below:

On the Title Page, Item [54] delete "APPARATUS FOR PROVIDING RADIANT ENERGY" and substitute therefor --ARRAY OF MONOCHROMATIC OPTOELECTRONIC DEVICES THAT PRODUCES RADIANT ENERGY--.

Signed and Sealed this

Seventh Day of June, 1994

Attest:

BRUCE LEHMAN

Attesting Officer

Commissioner of Patents and Trademarks